Figure 1:
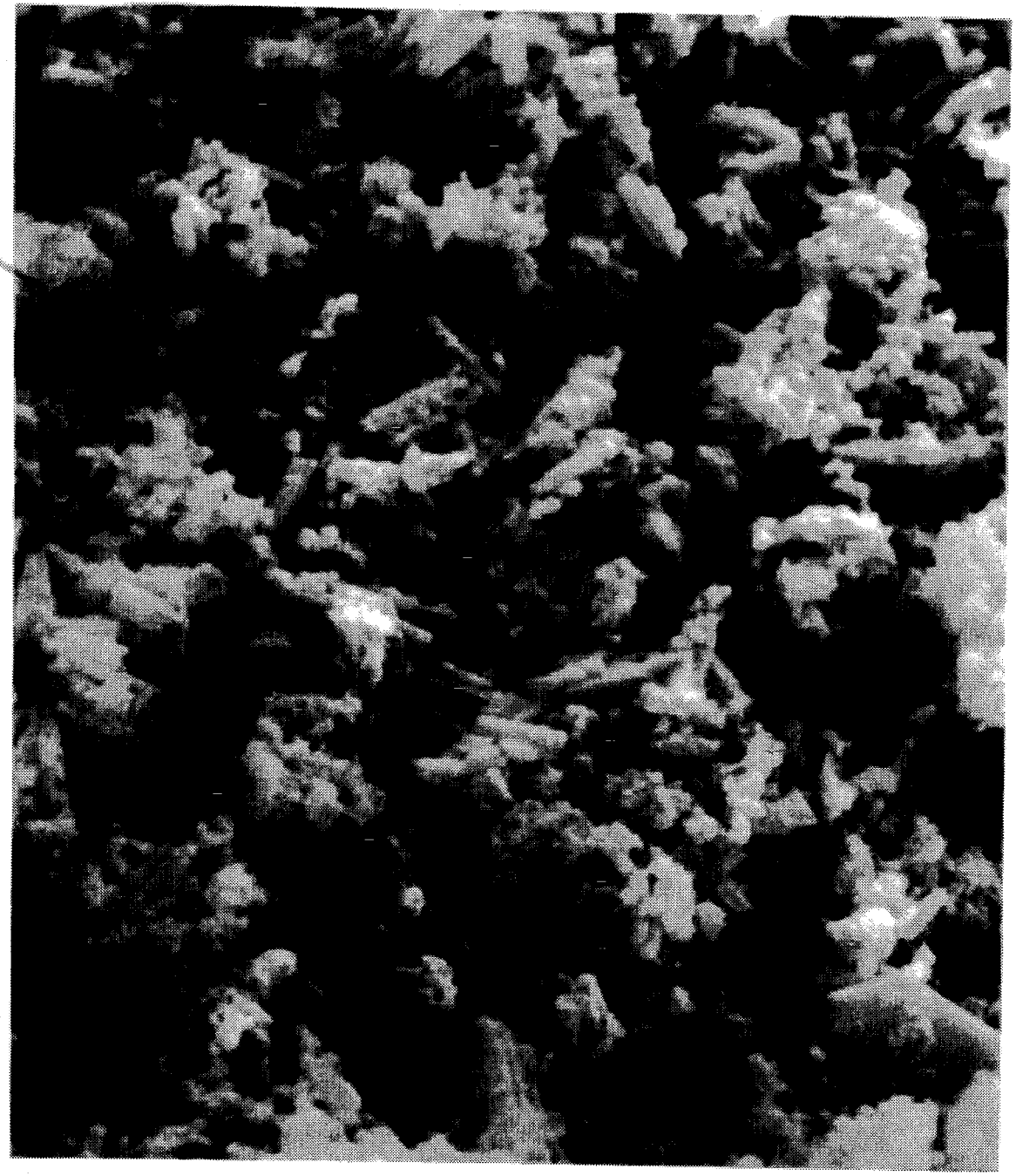

United States Patent [19]
Winston

[11] Patent Number: 5,482,701
[45] Date of Patent: Jan. 9, 1996

[54] MICROPOROUS ALKALI METAL BICARBONATE

[75] Inventor: Anthony E. Winston, East Brunswick, N.J.

[73] Assignee: Church & Dwight Co., Inc., Princeton, N.J.

[21] Appl. No.: 56,485

[22] Filed: May 3, 1993

[51] Int. Cl.⁶ .................................................. A61K 7/32
[52] U.S. Cl. .......................... 424/65; 424/421; 424/489; 424/490
[58] Field of Search ................ 424/65, 421, 489, 424/490

[56] References Cited

U.S. PATENT DOCUMENTS

| | | | |
|---|---|---|---|
| 2,378,147 | 6/1945 | McGeorge et al. | 167/72 |
| 4,587,120 | 5/1986 | Ozawa et al. | 424/57 |
| 4,867,988 | 9/1989 | Chernack | 424/490 |
| 5,147,631 | 9/1992 | Glajch et al. | 424/9 |
| 5,158,756 | 10/1992 | Ogawa et al. | 423/309 |

FOREIGN PATENT DOCUMENTS 1088428  10/1980  Canada .................................. 424/65

*Primary Examiner*—Alan L. Rotman
*Assistant Examiner*—Ba K. Trinh
*Attorney, Agent, or Firm*—Charles B. Barris

[57] ABSTRACT

This invention provides microporous alkali metal bicarbonate, which can contain an absorbed gaseous, liquid or solid phase as an encapsulated ingredient. A present invention microporous bicarbonate composition has utility as a lightweight deodorant ingredient in a cosmetic stick or roll-on product. This permits the solid organic matrix and dispersed deodorant particle phases to have densities which are sufficiently matched to prevent setting of the dispersed particles during manufacture, and to provide a cosmetic stick or roll-on product with dimensional stability.

5 Claims, 1 Drawing Sheet

5,482,701

MICROPOROUS ALKALI METAL BICARBONATE

CROSS-REFERENCE TO RELATED PATENT APPLICATION

The subject matter of the present invention is related to that described in patent application Ser. No. 07/986,810, filed Dec. 8, 1992.

Sodium bicarbonate has long been recognized for its deodorant properties, and has commonly been used as a household deodorant. Plain powdered sodium bicarbonate, or sodium bicarbonate diluted with talc or other filler, has been used as an underarm deodorant as disclosed in U.S. Pat. No. 4,382,079. Other publications which describe cosmetic stick compositions containing a bicarbonate deodorant include U.S. Pat. No. 4,822,602 and U.S. Pat. No. 4,832,945.

However, the development of a practical and effective deodorant composition in cosmetic stick form which is capable of consumer acceptability is not readily achievable. Because sodium and potassium bicarbonate have only limited solubility in water, alcohol and other solvents, the preparation of a composition suitable for dispensing in cosmetic stick form has involved many processing obstacles. Also, the dimensional stability of the cosmetic stick containing sodium bicarbonate, and the esthetic appearance and the "feel" on the skin, are just a few of the additional difficulties encountered in the preparation of a low residue deodorant cosmetic stick product.

Another significant problem associated with the incorporation of a bicarbonate deodorant ingredient in a cosmetic stick formulation is the tendency for the high density bicarbonate salt particles to settle in the fluid medium during processing. The problem of bicarbonate particle settling is particularly severe when the bicarbonate powder is a deodorant ingredient in a liquid roll-on cosmetic formulation.

United States patents of background interest with respect to the present invention embodiments described herein include U.S. Pat. Nos. 2,378,147; 4,587,120; 5,147,631; and 5,158,756.

There is continuing interest in the development of improved cosmetic stick and roll-on products which exhibit deodorant activity, and in novel ingredients for their preparation.

Accordingly, it is an object of this invention to provide a novel form of alkali metal bicarbonate powder.

It is another object of this invention to provide alkali metal bicarbonate powder which has the capacity to absorb and encapsulate a gaseous, liquid or solid phase.

It is another object of this invention to provide a homogeneous deodorant cosmetic stick or roll-on product which contains a dispersed phase of particulate bicarbonate deodorant ingredient in a solid organic matrix phase, and which phases are density matched to prevent settling of the dispersed particles.

It is a further object of this invention to provide a cosmetic stick or roll-on product which contains microporous bicarbonate deodorant, and is characterized by excellent esthetics and cosmetic properties.

Other objects and advantages of the present invention shall become apparent from the accompanying description and examples.

DESCRIPTION OF THE INVENTION

One or more objects of the present invention are accomplished by the provision of microporous alkali metal bicarbonate powder comprising particles having an average particle size between about 0.1–50 microns, a surface area between about 5–20 square meters per gram, an average pore size between about 10–500 nanometers, and a total pore volume between about 0.1–2 cubic centimeters per gram.

A microporous powder of the present invention is composed of particles which comprise sodium bicarbonate or potassium bicarbonate or a mixture thereof.

The alkali metal bicarbonate particles typically have an open interconnected pore structure. Depending on the method of preparation, the alkali metal bicarbonate particles can consist of an agglomerate or cohesive aggregate of primary fine crystallites.

The term "particle size" as employed herein refers to the largest size dimension of a particle.

FIG. 1 is a Scanning Electron Microscope photomicrograph of agglomerated sodium bicarbonate crystallites. The mean average particle size of the primary crystallites is about 0.5–2 microns and the mean average agglomerate size is about 4–12 microns.

The agglomerated crystallites are a cohesive aggregate of crystallites which consist of an open structure of interconnected microporous voids between the agglomerated particles.

Alkali metal bicarbonate in the form of agglomerated crystallites with a microporous matrix can be prepared by a precipitation method. Primary particle and agglomerate size can be controlled by varying the processing conditions.

A typical procedure involves the dissolution of alkali metal bicarbonate in water at 20°–40° C., and the subsequent addition of a water-soluble organic solvent to the aqueous solution to precipitate the alkali metal bicarbonate as agglomerated crystallites having a structure similar to the FIG. 1 photomicrograph configuration.

Agglomerated crystallites having primary particles of submicron dimensions can be obtained by a variation of the precipitation method. In the process embodiment described above, the aqueous solution of alkali metal bicarbonate is added incrementally with stirring to a volume of a water-soluble organic solvent such as methanol. As an additional processing variable, the size of the primary particles can be changed by varying the concentration of alkali metal bicarbonate in the aqueous solution.

The present invention further contemplates microporous alkali metal bicarbonate powders of larger particle size which can be prepared by employing other combinations of processing conditions.

In another embodiment this invention provides microporous alkali metal bicarbonate powder comprising particles having an average particle size between about 50–600 microns, a surface area between about 2–30 square meters per gram, an average pore size between about 5–600 nanometers, and a total pore volume between about 0.1–5 cubic centimeters per gram.

Microporous alkali metal bicarbonate of larger particle size can be prepared by coprecipitating a mixture of alkali metal bicarbonate and ammonium bicarbonate from an aqueous solution. Microporosity can be introduced in the alkali metal bicarbonate by removal of the ammonium bicarbonate from the coprecipitated particles. This can be accomplished by heating the coprecipitated solids to a temperature above about 60° C., preferably under reduced pressure conditions. The elevated temperature decomposes the ammonium bicarbonate into ammonia, water and carbon dioxide volatiles.

As an alternative procedure, the readily water-soluble ammonium bicarbonate can be removed by slurrying an alkali metal bicarbonate/ammonium bicarbonate coprecipitate in a saturated aqueous solution of the alkali metal bicarbonate, and recovering the residual microporous alkali metal bicarbonate solids. The selective dissolution of the ammonium bicarbonate can be moderated by the inclusion of a minor quantity of water-soluble organic solvent in the aqueous medium.

In the coprecipitated solids described above, the content of the ammonium bicarbonate relative to the alkali metal bicarbonate can vary in the range between about 0.5–30 weight percent, based on the weight of coprecipitated solids.

The apparent particle density of microporous alkali metal bicarbonate particles varies directly with total pore volume content of the particles. Alkali metal bicarbonate particles having a total pore volume of about 0.1–2 cubic centimeters per gram can have a corresponding apparent particle density which is between about 30–96 percent of the density of nonporous alkali metal bicarbonate crystallites. When the total pore volume of the alkali metal bicarbonate particles is about 0.1–5 cubic centimeters per gram, the apparent particle density can be between about 17–96 percent of the density of the corresponding nonporous particles.

The apparent particle density of microporous alkali metal bicarbonate is the average weight of the solid crystal matrix plus entrapped air or gas in the pore volume divided by the total volume of the crystal matrix and the pore structure. Thus, a particulate solid with a crystal density of 2.29 g/cc having a pore volume of 1.0 cc/g has an apparent particle density of 0.69 g/cc. The apparent particle density of microporous alkali metal bicarbonate can vary in the range between about 0.7–2 grams per cubic centimeter.

The crystal density of a particulate solid is the weight of solid crystal divided by the volume occupied by the crystal. This measurement excludes the weight and volume of any pore content. The crystal density of each chemical compound or allotrope is a fixed value for that species.

The crystal density of sodium bicarbonate is 2.2 g/cc, and can be measured by means of a pycnometer procedure using a fluid which permeates any pore volume in the crystalline solid. The apparent particle density is measured by using a similar procedure with a fluid such as mercury which does not permeate the pore volume of the particles.

Standard procedures are followed for measurement of the other physical properties of fine particles.

Surface area is determined by the nitrogen absorption method of Brunauer, Emmett and Teller (BET).

Particle size is determined by transmission electron microscopy, or by X-ray diffractometry.

The volume average pore size distribution and total intruded volume are determined by mercury porosimetry, and calculated in accordance with an equation as described in U.S. Pat. No. 5,094,829.

Microporous alkali metal bicarbonate has a versatile combination of properties which has advantage in a broad range of applications.

Microporous alkali metal bicarbonate is readily amenable to the absorption of a gaseous, liquid or solid phase which becomes encapsulated in the open pore volume.

Illustrative of an encapsulated phase ingredient are biologically active compounds, odorants, deodorants, antiperspirants, fertilizers, and the like. The encapsulated phase can occupy a small portion of the total intruded volume, or it can fill essentially all of the voids in the microporous alkali metal bicarbonate.

A gas phase such as carbon dioxide can be introduced into the matrix of microporous alkali metal bicarbonate which is contained in a sealed vessel, by vacuum evacuation of the vessel followed by repressuring with a carbon dioxide environment. A liquid phase such as a fragrance can be introduced by suspending alkali metal bicarbonate powder in the liquid medium to effect absorption of the liquid into the microporous structure.

A solid phase such as urea or Triclosan can be introduced as a solution in an organic solvent followed by removal of the organic solvent from the microporous structure. If a solid ingredient such as urea is sufficiently low melting, then the encapsulation can be accomplished by suspension of the microporous alkali metal bicarbonate in a fluid melt of the ingredient.

A further aspect of the present invention is the provision of a deodorant such as microporous alkali metal bicarbonate which has a content of a fragrance ingredient as an encapsulated phase. This type of composition has utility as a solid suspension ingredient which is density matched with the organic matrix of a cosmetic stick or roll-on deodorant or antiperspirant-deodorant product, and provides controlled release of fragrance ingredient under application conditions.

When the solid organic matrix and dispersed inorganic particle phases have densities which are sufficiently matched, settling of the dispersed particles during manufacture is prevented, and a cosmetic stick or roll-on product with dimensional stability is produced.

Nonporous alkali metal bicarbonate deodorant compounds have a similar crystal density and apparent particle density which is about 2.2 grams per cubic centimeter. If such high density particulate ingredients are suspended in an organic matrix having a density of about one gram per cubic centimeter, the particles have a tendency to settle out of the organic matrix, and the resultant cosmetic stick or roll-on product is inhomogeneous and dimensionally unstable.

Density matching of inorganic and organic phases is a significant factor in cosmetic stick and roll-on products. The present invention provides lower density alkali metal bicarbonate deodorant ingredient which closely matches the density of the organic matrix of a cosmetic stick or roll-on product.

When there is density matching of organic matrix and dispersed particle phases, a cosmetic stick or roll-on product has improved dimensional stability, and better esthetic appearance and "feel" when applied to human skin.

The following Examples are further illustrative of the present invention. The components and specific ingredients are presented as being typical and various modifications can be derived in view of the foregoing disclosure within the scope of the invention.

EXAMPLE I

This Example illustrates the preparation of microporous sodium bicarbonate which corresponds to the agglomerated crystallites represented in the FIG. 1 SEM micrograph.

A saturated solution of sodium bicarbonate in water is prepared. The solution is added dropwise to a stirred volume of cold methanol solvent, until 10% by volume has been admixed. The resultant crystalline precipitate is collected by filtration, and dried under vacuum at 60° C.

The primary acicular particles have a length of about 1–2 microns. The agglomerated crystallite particles have a diameter of about 5–8 microns, a surface area of about 8 square meters per gram, a pore size of about 80–120 nanometers, and a total pore volume of about 0.6 cubic centimeters per gram.

If the methanol solvent is added dropwise to the saturated sodium bicarbonate solution with stirring, the primary crystallite and agglomerated crystallite particles of the recovered crystalline precipitate are larger in dimensions as compared to the product of the first precipitation procedure described above.

EXAMPLE II

This Example illustrates a pilot-plant procedure for the preparation of an antiperspirant-deodorant cosmetic stick product which utilizes a microporous alkali metal bicarbonate ingredient in accordance with the present invention.

A stainless steel tank is provided which is equipped with turbine agitation.

Silicone oil DC 245 (600 lbs, Dow Corning) is charged to the mixing tank. Agitation (55–65 RPM) is initiated, and heating the liquid medium to 176° F. is commenced.

During the heating period, the following order of ingredients are added to the stirred liquid medium:

|  | lbs. |
| --- | --- |
| diisopropyl adipate | 60 |
| PPG 14 butyl ether (Americol) | 40 |
| stearyl alcohol | 340 |
| castor wax (MP-70) | 60 |
| eicosanol | 10 |
| PEG 600 distearate (Mazer) | 40 |

The mixture is stirred at 176° F. for about 30 minutes until the ingredients are melted and the liquid medium is homogeneous. The stirring speed is reduced to about 35 RPM, then Cab-o-sil M-5 (15 lbs, Cabot) and aluminum zirconium tetrachlorohydrex glycine (480 lbs, Reheis) are added. The temperature is maintained at 176° F. for about 40 minutes until the fluid medium is uniform, and then the temperature is lowered to 124° F.

Microporous sodium bicarbonate powder (120 lbs, Church & Dwight) and a fragrance (6 lbs, IFF 567-AT) respectively are added with stirring to Silicone oil DC 245 (245 lbs, Dow Corning) in a second mixing tank at a temperature of 124° F. to form a homogeneous suspension medium. The microporous sodium bicarbonate powder is prepared by a precipitation method as described in Example I, and has an apparent particle density of about 0.9 gram per cubic centimeter.

The contents of the two mixing tanks which contain heated fluid medium are transferred to separate fill tanks through a Greer mill, and the fill tanks are connected to a mixing and dispensing nozzle device, of the type described in U.S. Pat. No. 5,094,276. The nozzle device is adapted for homogeneously blending the two separate streams of fluid media, and dispensing a predetermined quantity of the blended fluid.

Plastek 2 oz. bottom-fill stick containers are filled with the blended fluid. The container contents are cooled to a room temperature solid stick over a period of about 45 minutes. The average hardness value of the solid sticks is 7 (ASTM Method D5).

A second deodorant cosmetic stick product is prepared by eliminating the antiperspirant ingredient, and increasing the quantity of microporous sodium bicarbonate ingredient from 120 lbs to 160 lbs in the above described manufacturing process.

What is claimed is:

1. Microporous alkali metal bicarbonate powder comprising particles having an average particle size between about 0.1–50 microns, a surface area between about 5–20 square meters per gram, an average pore size between about 10–500 nanometers, and a total pore volume between about 0.1–2 cubic centimeters per gram; and wherein the particles consist of agglomerated crystallites.

2. A microporous powder in accordance with claim 1 wherein the alkali metal bicarbonate is sodium bicarbonate or potassium bicarbonate.

3. A microporous powder in accordance with claim 1 wherein the particles have an open interconnected pore structure.

4. A microporous powder in accordance with claim 1 wherein the particles have a density between about 40–90 percent of the density of corresponding nonporous particles.

5. A microporous powder in accordance with claim 1 wherein the particles have a content of an encapsulated gaseous, liquid or solid phase.

* * * * *